US011759658B2

(12) United States Patent
Strzelecki et al.

(10) Patent No.: US 11,759,658 B2
(45) Date of Patent: Sep. 19, 2023

(54) MOTION ARTIFACT REDUCTION IN COMPUTED TOMOGRAPHY

(71) Applicant: SIEMENS HEALTHINEERS INTERNATIONAL AG, Palo Alto, CA (US)

(72) Inventors: Adam Michal Strzelecki, Daettwil (CH); Dieter Marc Seghers, Zürich (CH); Igor Peterlik, Kuenten (CH); Mathieu Plamondon, Glattbrugg (CH); Pascal Paysan, Basel (CH); Peter N Munro, Daettwil (CH); Philippe Messmer, Zürich (CH)

(73) Assignee: SIEMENS HEALTHINEERS INTERNATIONAL AG

( * ) Notice: Subject to any disclaimer, the term of this patent is extended or adjusted under 35 U.S.C. 154(b) by 189 days.

(21) Appl. No.: 17/218,484

(22) Filed: Mar. 31, 2021

(65) Prior Publication Data
US 2022/0313181 A1 Oct. 6, 2022

(51) Int. Cl.
*A61N 5/10* (2006.01)
*G06T 7/11* (2017.01)
(Continued)

(52) U.S. Cl.
CPC .......... *A61N 5/1064* (2013.01); *A61B 6/5264* (2013.01); *A61N 5/1049* (2013.01);
(Continued)

(58) Field of Classification Search
CPC .......... A61B 2090/3904; A61N 5/1049; A61N 2005/1051–1063; G06T 7/10–11;
(Continued)

(56) References Cited

U.S. PATENT DOCUMENTS

2012/0308101 A1 12/2012 Zeng et al.
2014/0376791 A1 12/2014 Heigl et al.
(Continued)

OTHER PUBLICATIONS

International Search Report and Written Opinion of the International Searching Authority, International application No. PCT/EP2022/058591, dated Aug. 16, 2022.

*Primary Examiner* — Emily C Terrell
*Assistant Examiner* — Emmanuel Silva-Avina
(74) *Attorney, Agent, or Firm* — SU IP CONSULTING

(57) ABSTRACT

A reconstructed volume of a region of patient anatomy is processed to reduce motion artifacts in the reconstructed volume. Autosegmentation of high-contrast structures present in an initial reconstructed volume is performed to generate a 3D representation of the high-contrast structures. 2D mask projections are generated by performing forward projection on the 3D representation, where each 2D mask projection includes location information indicating pixels that correspond to the high-contrast structures during the forward projection process. The acquired 2D projections are modified via in-painting to generate corrected 2D projections, where the acquired 2D projections are modified using information from the 2D mask projections. For example, pixels in the acquired 2D projections that are associated with high-contrast moving structures are replaced with low-contrast pixels. These corrected 2D projections are used to produce an improved reconstructed volume with fewer and/or less visually prominent motion artifacts.

18 Claims, 9 Drawing Sheets

(51) Int. Cl.
*A61B 6/00* (2006.01)
*G06T 5/00* (2006.01)
*G06T 11/00* (2006.01)

(52) U.S. Cl.
CPC ............... *G06T 5/005* (2013.01); *G06T 7/11* (2017.01); *G06T 11/008* (2013.01); *A61B 6/4014* (2013.01); *A61N 2005/1061* (2013.01); *G06T 2200/08* (2013.01); *G06T 2207/10081* (2013.01); *G06T 2207/30096* (2013.01); *G06T 2207/30204* (2013.01)

(58) Field of Classification Search
CPC ............... G06T 5/005; G06T 2200/08; G06T 2207/10081; G06T 2207/30204; G06T 2211/421; G06T 11/008
USPC ........................................................ 382/174
See application file for complete search history.

(56) References Cited

U.S. PATENT DOCUMENTS

| | | | |
|---|---|---|---|
| 2015/0029178 A1 | 1/2015 | Claus et al. | |
| 2016/0007948 A1* | 1/2016 | Isola | A61B 6/5258 382/131 |
| 2019/0059840 A1* | 2/2019 | Fouras | A61B 6/507 |
| 2019/0175131 A1 | 6/2019 | Duewer | |
| 2021/0264591 A1* | 8/2021 | Park | G06T 7/0012 |

\* cited by examiner

MOTION ARTIFACT REDUCTION IN COMPUTED TOMOGRAPHY

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three-dimensional image of the target tissue and surrounding area. From such imaging, the size and mass of the target tissue can be estimated, a planning target volume determined, and an appropriate treatment plan generated.

So that the prescribed dose is correctly supplied to the planning target volume (i.e., the target tissue) during radiation therapy, the patient should be correctly positioned relative to the linear accelerator that provides the radiation therapy. Typically, dosimetric and geometric data are checked before and during the treatment, to ensure correct patient placement and that the administered radiotherapy treatment matches the previously planned treatment. This process is referred to as image guided radiation therapy (IGRT), and involves the use of an imaging system to view target tissues immediately before or while radiation treatment is delivered to the planning target volume. IGRT incorporates imaging coordinates from the treatment plan to ensure the patient is properly aligned for treatment in the radiation therapy device.

SUMMARY

According to various embodiments, a reconstructed volume of a region of patient anatomy is processed so that motion artifacts in the reconstructed volume are reduced. Specifically, in some embodiments, autosegmentation of high-contrast structures present in an initial reconstructed volume is performed to generate a 3D representation of the high-contrast structures. 2D mask projections are generated by performing forward projection on the 3D representation, where each 2D mask projection includes location information indicating pixels that correspond to (and are blocked by) the high-contrast structures during the forward projection process. The acquired 2D projections on which the initial reconstructed volume is based are each modified with an in-painting process to generate corrected 2D projections of the region of patient anatomy, where the acquired 2D projections are modified using information from the 2D mask projections. That is, pixels in the acquired 2D projections that are associated with high-contrast moving structures are replaced with low-contrast pixels (for example using interpolation), which reduces inconsistencies between the projections. These corrected 2D projections are in turn used to produce an improved reconstructed volume with fewer and/or less visually prominent motion artifacts. In some embodiments, the resulting volume is processed and forward-projected to further improve the initial reconstructed volume.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
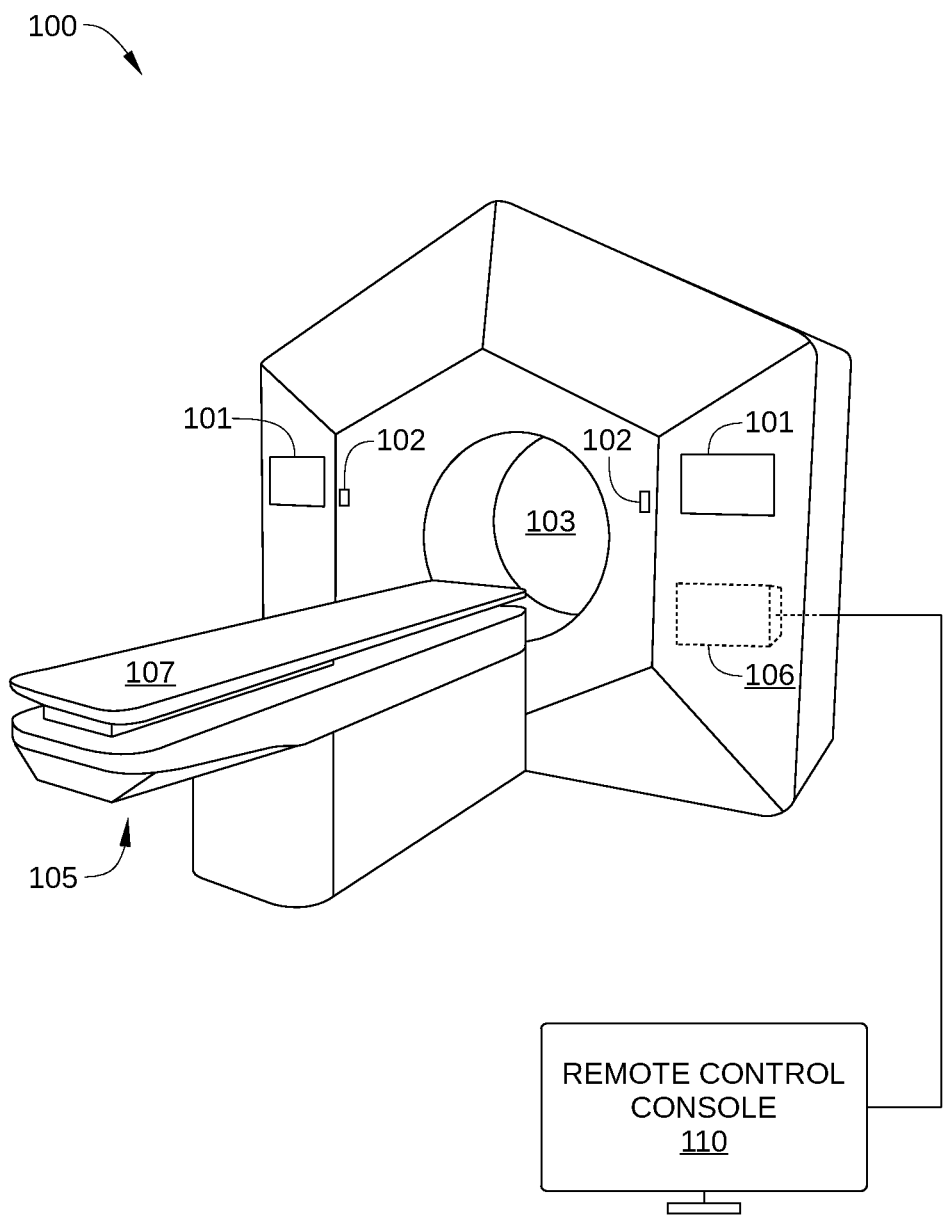
FIG. 1 is a perspective view of a radiation therapy system that can beneficially implement various aspects of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

Image guided radiation therapy (IGRT) is used to treat tumors in areas of the body that are subject to voluntary movement, such as the lungs, or involuntary movement, such as organs affected by peristalsis, gas motion, muscle contraction and the like. IGRT involves the use of an imaging system to view target tissues (also referred to as the "target volume") immediately before or while radiation treatment is delivered thereto. In IGRT, image-based coordinates of the target volume from a previously determined treatment plan are compared to image-based coordinates of the target volume determined immediately before or during the application of the treatment beam. In this way, changes in the surrounding organs at risk and/or motion or deformation of the target volume relative to the radiation therapy system can be detected. Consequently, dose limits to organs at risk are accurately enforced based on the daily position and shape, and the patient's position and/or the treatment beam can be adjusted to more precisely target the radiation dose to the tumor. For example, in pancreatic tumor treatments, organs at risk include the duodenum and stomach. The shape and relative position of these organs at risk with respect to the target volume can vary significantly from day-to-day. Thus, accurate adaption to the shape and relative position of such organs at risk enables escalation of the dose to the target volume and better therapeutic results.

For reconstructions of patient anatomy surrounding a target volume, cone-beam computed tomography (CBCT) is often employed for generating the two-dimensional (2D) projections images from which the patient anatomy is reconstructed. However, the time required for completion of a CBCT-based acquisition is generally long enough that voluntary and/or involuntary motion of structures in the patient anatomy often occur during the course of image acquisition. Because three-dimensional (3D) reconstruction algorithms generally assume that a volume being reconstructed remains stationary during acquisition of the 2D projection images, the resulting 3D reconstructions are prone to suffer from data inconsistencies. For high-contrast structures, such as fiducial markers and air pockets, these inconsistencies can manifest visually as streak artifacts within the reconstructed volume. For example, such streaks may originate from the moving structure and radiate outward in the reconstructed volume.

These so-called "motion artifacts" are produced as a side-effect of the reconstruction algorithm trying to reconcile the measurements with a volume that has changed over time. The magnitude of such motion artifacts depends on both motion range and moving structure contrast. Thus, motion during the image acquisition of air pockets or other high-contrast structures is more likely to result in more prominent motion artifacts. Such motion might occur due to breathing movements, in which a large volume of the body moves, or to involuntary physiological changes or motion, in which displacements of high contrast structures (e.g., air pockets in the intestine) occur. In either case, significant motion artifacts may occur that degrade the quality of the reconstruction and the ability of accurately detect the current location of a target volume and/or critical structures adjacent to the target volume.

One approach for addressing such motion artifacts involves blurring the areas in the projection space where motion takes place during CBCT image acquisition. In some instances, this approach reduces the targeted motion artifacts, but typically also introduces other streaking artifacts. As a result, the benefits of such an approach are limited.

According to various embodiments, a reconstructed volume of a region of patient anatomy is processed so that motion artifacts in the reconstructed volume are reduced. Specifically, in some embodiments, autosegmentation of high-contrast structures present in an initial reconstructed volume is performed to generate a 3D representation of the high-contrast structures. 2D mask projections are generated by performing forward projection on the 3D representation, where each 2D mask projection includes location information indicating pixels that correspond to (and are blocked by) the high-contrast structures during the forward projection process. The acquired 2D projections on which the initial reconstructed volume is based are each modified with an in-painting process to generate corrected 2D projections of the region of patient anatomy, where the acquired 2D projections are modified using information from the 2D mask projections. That is, pixels in the acquired 2D projections that are associated with high-contrast moving structures are replaced with low-contrast pixels (for example using interpolation), which reduces inconsistencies between the projections. These corrected 2D projections are in turn used to produce an improved reconstructed volume with fewer and/or less visually prominent motion artifacts. In some embodiments, the resulting volume is post-processed and forward-projected to further improve the initial reconstructed volume.

FIG. 1 is a perspective view of a radiation therapy system 100 that can beneficially implement various aspects of the present disclosure. Radiation therapy (RT) system 100 is a radiation system configured to detect intra-fraction motion in near-real time using X-ray imaging techniques. Thus, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, one or more kilovolt (kV) X-ray sources, one or more X-ray imagers, and, in some embodiments, an MV electronic portal imaging device (EPID). By way of example, radiation therapy system 100 is described herein configured with a circular gantry. In other embodiments, radiation therapy system 100 can be configured with a C-gantry capable of infinite rotation via a slip ring connection.

Generally, RT system 100 is capable of kV imaging of a target volume immediately prior to or during application of an MV treatment beam, so that an IGRT and/or an intensity-modulated radiation therapy (IMRT) process can be performed using X-ray imaging. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location.

Figure 2:
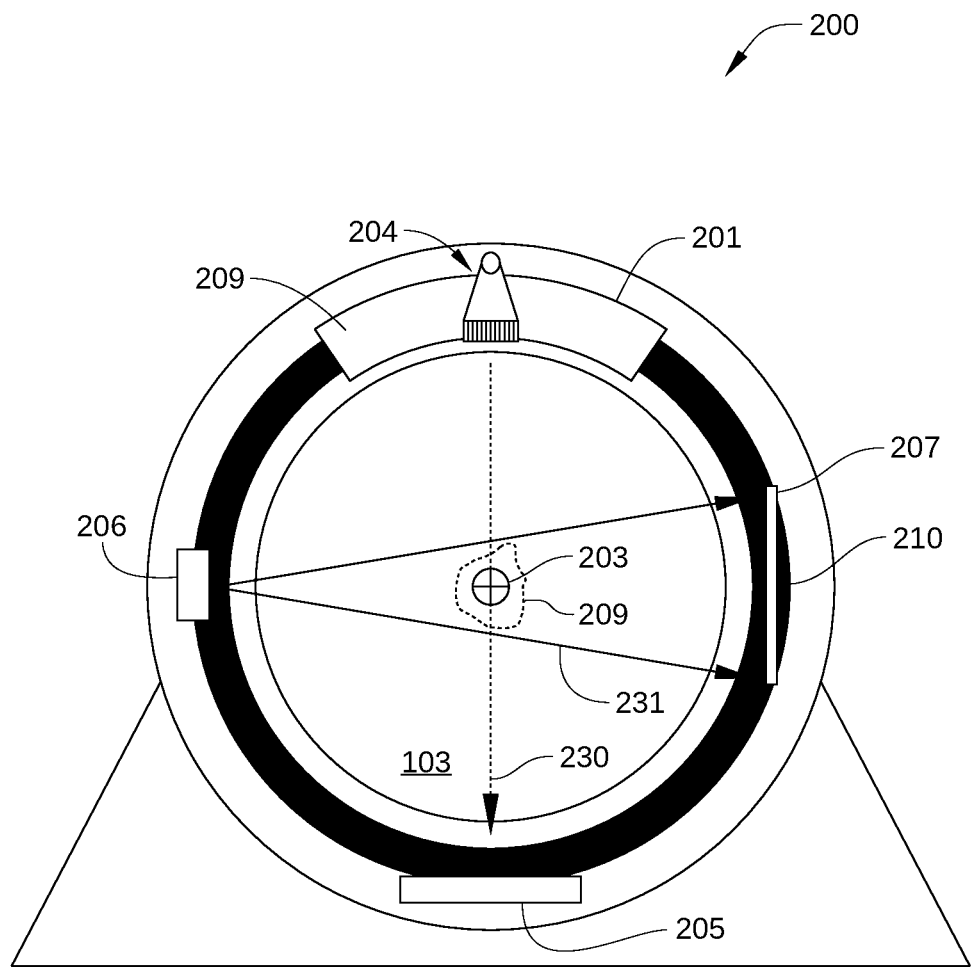
FIG. 2 schematically illustrates a drive stand and gantry of the radiation therapy system of FIG. 1, according to various embodiments.

FIG. 2 schematically illustrates a drive stand 200 and gantry 210 of RT system 100, according to various embodiments. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT treatment system 110, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT treatment system 110, gantry 210 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons, protons, and/or other heavy charged particles, ultra-high dose rate X-rays (e.g., for FLASH radiotherapy) or microbeams for microbeam radiation therapy) and EPID 205 is configured to acquire X-ray images with treatment beam 230. Imaging X-ray source 206 is configured to direct a conical beam of X-rays, referred to herein as imaging X-rays 231, through an isocenter 203 of RT system 100 to X-ray imager 207, and isocenter 203 typically corresponds to the location of a target volume 209 to be treated. In the embodiment illustrated in FIG. 2, X-ray imager 207 is depicted as a planar device, whereas in other embodiments, X-ray imager 207 can have a curved configuration.

X-ray imager 207 receives imaging X-rays 231 and generates suitable projection images therefrom. According to certain embodiments, such projection images can then be employed to construct or update portions of imaging data for a digital volume that corresponds to a three-dimensional (3D) region that includes target volume 209. That is, a 3D image of such a 3D region is reconstructed from the projection images. In some embodiments, cone-beam computed tomography (CBCT) and/or digital tomosynthesis (DTS) can be used to process the projection images generated by X-ray imager 207. CBCT is typically employed to acquire projection images over a relatively long acquisition arc, for example over a rotation of 180° or more of gantry 210. As a result, a high-quality 3D reconstruction of the imaged volume can be generated. CBCT is often employed at the beginning of a radiation therapy session to generate a set-up 3D reconstruction. For example, CBCT may be employed immediately prior to application of treatment beam 230 to generate a 3D reconstruction confirming that target volume 209 has not moved or changed shape. Alternatively, or additionally, in some embodiments, partial-data reconstruction is performed by RT system 100 during portions of an IGRT or IMRT process in which partial image data is employed to generate a 3D reconstruction of target volume 209. For example, as treatment beam 230 is directed to isocenter 203 while gantry 210 rotates through a treatment arc, DTS image acquisitions can be performed to generate image data for target volume 209. Because DTS image acquisition is performed over a relatively short acquisition arc, for example between about 10° and 60°, near real-time feedback for the shape and position of target volume 209 can be provided by DTS imaging during the IGRT process.

In the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source. One such embodiment is illustrated in FIG. 3.

Figure 3:
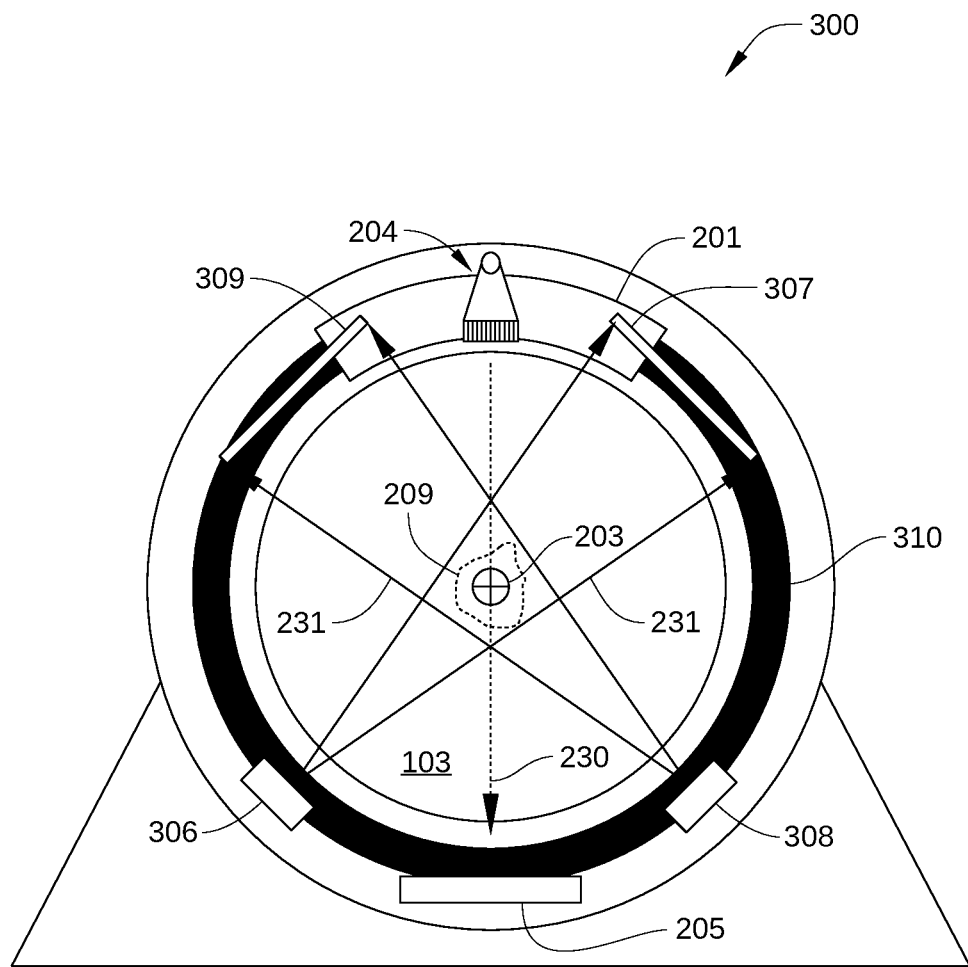
FIG. 3 schematically illustrates a drive stand and a gantry of the radiation therapy system of FIG. 1, according to various embodiments.

FIG. 3 schematically illustrates a drive stand 300 and gantry 310 of RT system 100, according to various embodiments. Drive stand 300 and gantry 310 are substantially similar in configuration to drive stand 200 and gantry 210 in FIG. 2, except that the components of RT system 100 that are mounted on gantry 310 include a first imaging X-ray source 306, a first X-ray imager 307, a second imaging X-ray source 308, and a second X-ray imager 309. In such embodiments, the inclusion of multiple X-ray imagers in RT system 100 facilitates the generation of projection images (for reconstructing the target volume) over a shorter image acquisition arc. For instance, when RT system 100 includes two X-ray imagers and corresponding X-ray sources, an image acquisition arc for acquiring projection images of a certain image quality can be approximately half that for acquiring projection images of a similar image quality with a single X-ray imager and X-ray source.

The projection images generated by X-ray imager 207 (or by first x-ray imager 307 and second X-ray imager 309) are used to construct imaging data for a digital volume of patient anatomy within a 3D region that includes the target volume. Alternatively or additionally, such projection images can be used to update portions of an existing imaging data for the digital volume corresponding to the 3D region. One embodiment of such a digital volume is described below in conjunction with FIG. 4.

Figure 4:
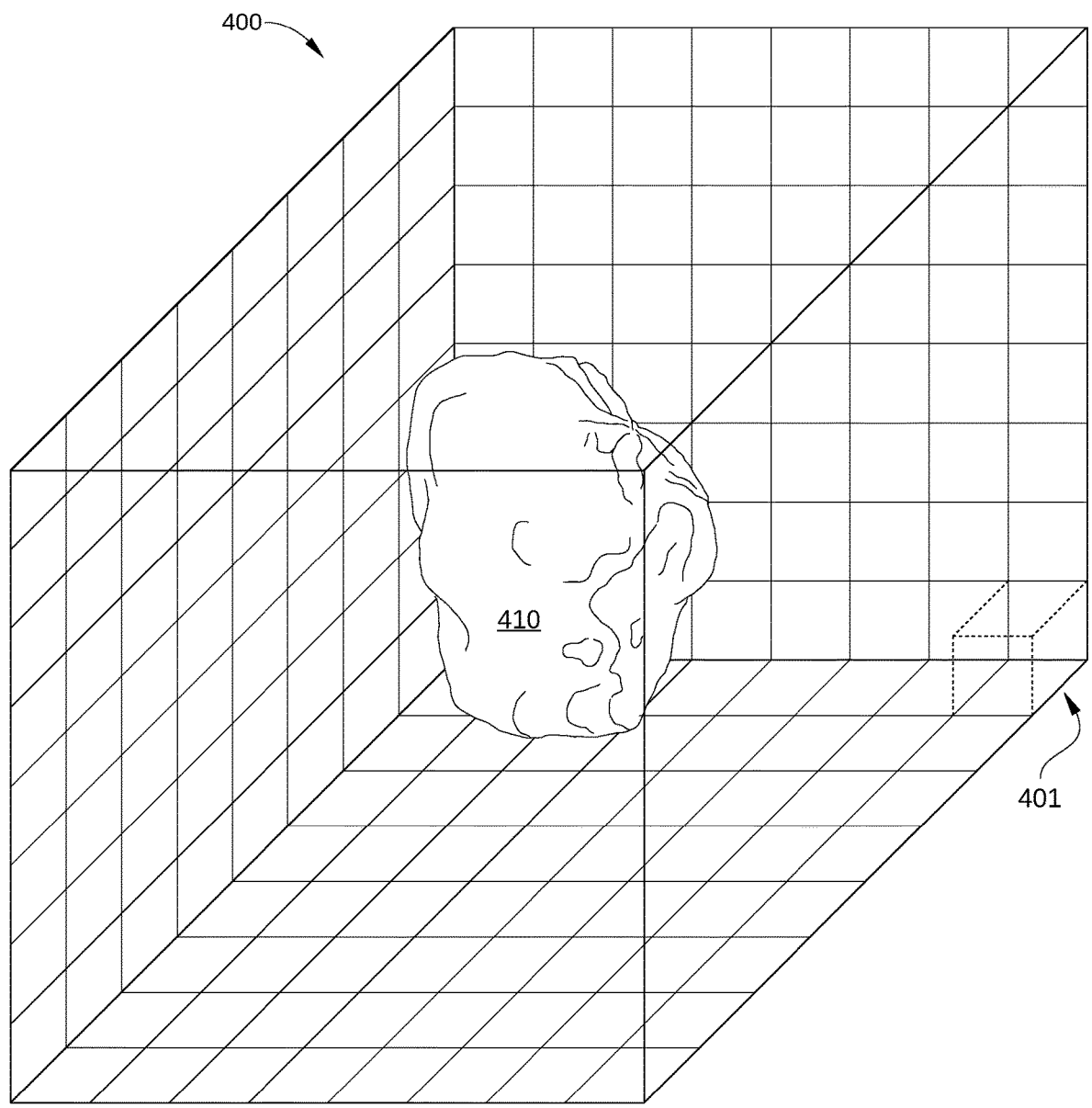
FIG. 4 schematically illustrates a digital volume that is constructed based on projection images generated by one or more X-ray images included in the radiation therapy system of FIG. 1, according to various embodiments.

FIG. 4 schematically illustrates a digital volume 400 that is constructed based on projection images generated by one or more X-ray imagers included in RT system 100, according to various embodiments. For example, in some embodiments, the projection images can be generated by a single X-ray imager, such as X-ray imager 207, and in other embodiments the projection images can be generated by multiple X-ray imagers, such as first x-ray imager 307 and second X-ray imager 309.

Digital volume 400 includes a plurality of voxels 401 (dashed lines) of anatomical image data, where each voxel 401 corresponds to a different location within digital volume 400. For clarity, only a single voxel 401 is shown in FIG. 4. Digital volume 400 corresponds to a 3D region that includes target volume 410. In FIG. 4, digital volume 400 is depicted as an 8×8×8 voxel cube, but in practice, digital volume 400 generally includes many more voxels, for example orders of magnitude more than are shown in FIG. 4.

For purposes of discussion, target volume 410 can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for sub-clinical disease spread, which is generally not imagable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of digital volume 400.

According to various embodiments described below, image information associated with each voxel 401 of digital volume 400 is constructed via projection images generated by the single or multiple X-ray imagers via a CBCT process. For example, such a CBCT process can be employed immediately prior to delivering treatment beam 230 to target volume 410, so that the location and shape of target volume 410 can be confirmed before treatment begins. In addition, according to various embodiments described below, image information associated with some or all of voxels 401 of digital volume 400 is updated via projection images generated by the single or multiple X-ray imagers via a DTS process. For example, such a DTS process can be employed after a portion of a planned treatment has begun and before the planned treatment has completed. In this way, the location and shape of target volume 410 can be confirmed while the treatment is underway. Thus, if a sufficient portion of the target volume 410 is detected to be extending outside a threshold region, the treatment can either be aborted or modified. In such an instance, modification of the treatment can be accomplished by adjusting patient position and/or the treatment beam.

Figure 5A:
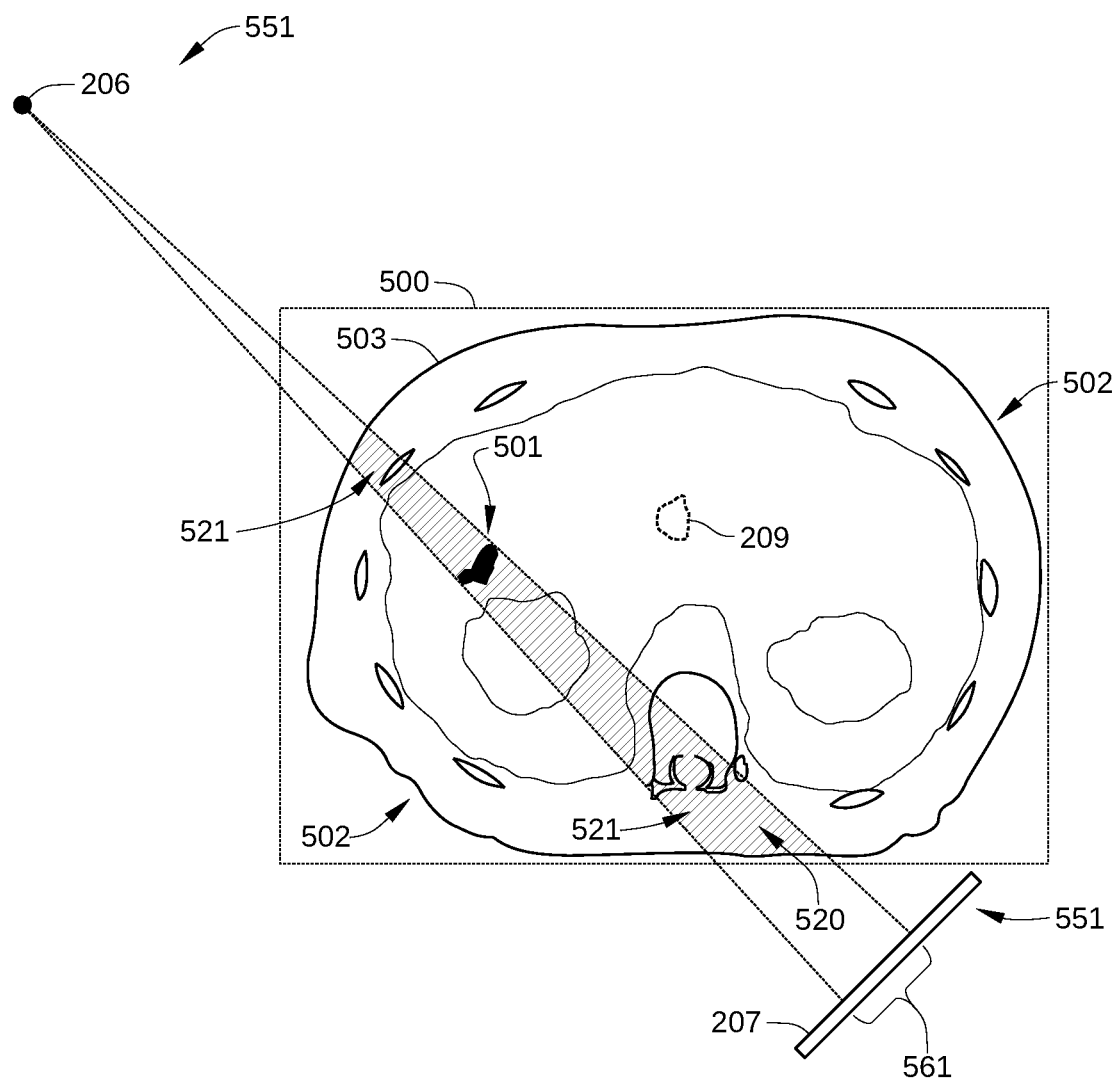
FIGS. 5A and 5B schematically illustrate the effect of a high-contrast moving structure on the imaging of a region of patient anatomy, according to an embodiment.
Figure 5B:
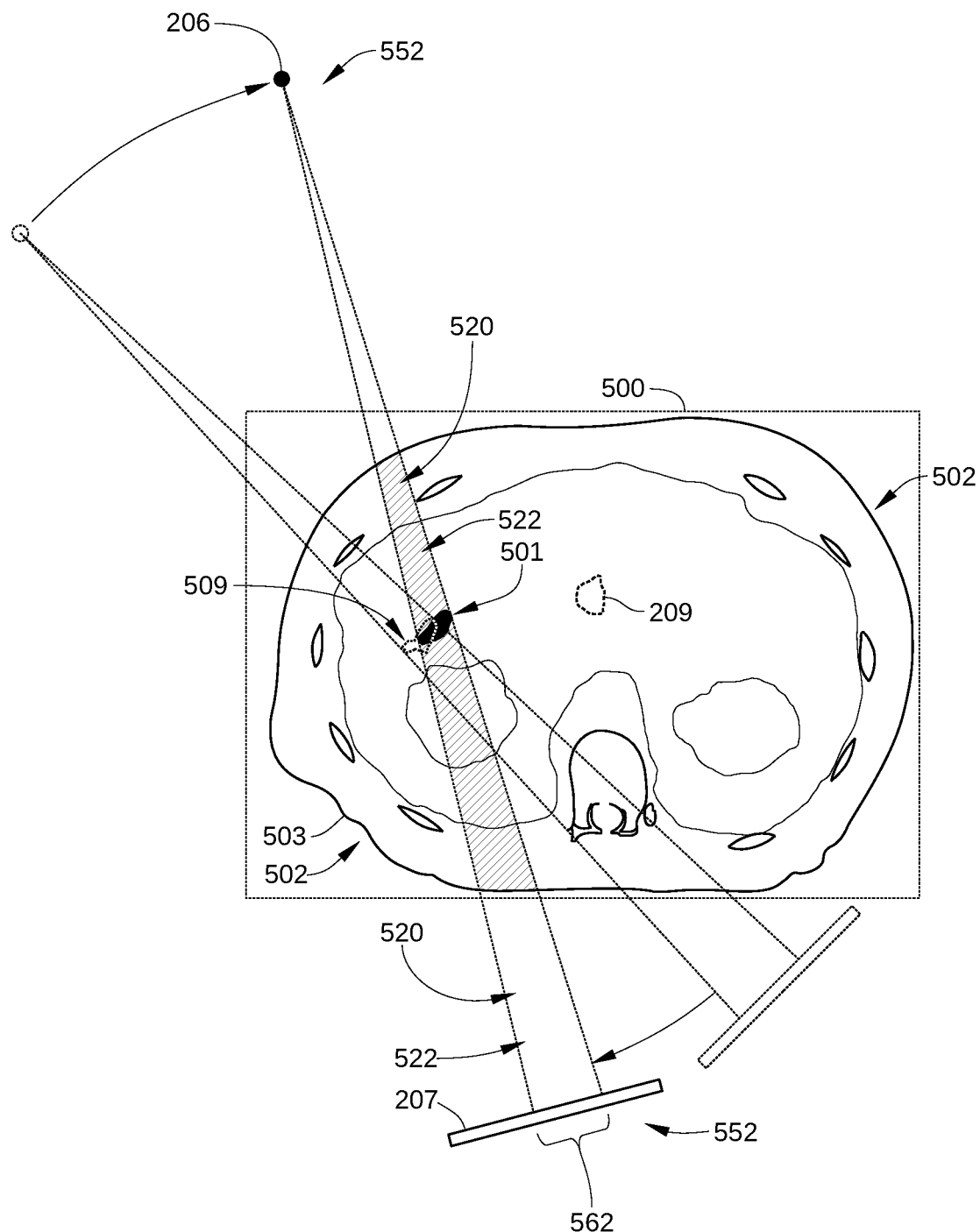

FIGS. 5A and 5B schematically illustrate the effect of a high-contrast moving structure 501 on the imaging of a region 502 of patient anatomy, according to an embodiment. Region 502 can be any technically feasible portion of patient anatomy, including the head, chest, abdomen, and the like. In the embodiment illustrated in FIGS. 5A and 5B, CBCT image acquisition is performed via imaging X-ray source 206 and X-ray imager 207 over a digital volume 500 that includes target volume 209 and extends to an edge surface 503 of region 502. In other embodiments, multiple X-ray sources and X-ray imagers can be employed. Alternatively or additionally, in some embodiments, digital volume 500 does not include all of edge surface 503, or does not include any portion of edge surface 503.

High-contrast moving structure 501 can be any portion of region 502 that appears as a high-contrast structure in an X-ray image of region 502 (and/or in a digital reconstruction of region 502) that moves a significant distance during a CBCT acquisition process to generate visible motion artifacts. For example, in some instances, high-contrast moving structure 501 is one of an air pocket, a gas bubble, a fiducial marker, surgical staple or other medical device, and/or the like. In other instances, high-contrast moving structure 501 can be any other portion of patient anatomy, material, or device that appears as a high-contrast structure in an X-ray image of region 502. FIG. 5A shows a 2D projection being acquired with imaging X-ray source 206 and X-ray imager 207 disposed at a first image acquisition position 551, and FIG. 5B shows a 2D projection being acquired with imaging X-ray source 206 and X-ray imager 207 disposed at a second image acquisition position 552.

For clarity of description, in FIGS. 5A and 5B, X-ray image acquisition by imaging X-ray source 206 and X-ray imager 207 is shown in only two possible image acquisition positions (first image acquisition position 551 and second image acquisition position 552). In practice, CBCT image acquisition is performed at a plurality of image acquisition positions around region 502 to enable generation of a digital reconstruction of digital volume 500. Further, in FIGS. 5A and 5B, X-ray imager 207 is viewed edge-on, and therefore is depicted as a one-dimensional imaging structure. In reality, X-ray imager 207 is typically configured to generate 2D projection images at each of a plurality of image acquisition locations.

As shown, high-contrast moving structure 501 appears in a different location on X-ray imager 207 for first image acquisition position 551 and for second image acquisition position 552. Specifically, when X-ray imager 207 is in first image acquisition position 551, high-contrast moving structure 501 appears in pixels 561 of X-ray imager 207, and when X-ray imager 207 is in second image acquisition position 552, high-contrast moving structure 501 appears in pixels 562 of X-ray imager 207. Thus, in the 2D projection acquired at first image acquisition position 551, pixels 561 are associated with high-contrast moving structure 501, and in the 2D projection acquired at second image acquisition position 552, pixels 562 are associated with high-contrast moving structure 501. In many instances, high-contrast moving structure 501 moves and/or changes shape between a first acquisition time (at which imaging X-ray source 206 and X-ray imager 207 are in first image acquisition position 551) and a second acquisition time (at which imaging X-ray source 206 and X-ray imager 207 are in second image acquisition position 552). For reference, an original size and shape 509 of high-contrast moving structure 501 is shown as dashed lines in FIG. 5B. It is noted that such changes in location and/or shape of high-contrast moving structure 501 over time can significantly contribute to visual artifacts and/or other inconsistencies when the 2D projection images are employed to reconstruct a 3D volume of region 502.

It is noted that the high contrast of high-contrast moving structure 501 generally obscures other information in blocked portions 520 (cross-hatched) of region 502, where blocked portions 520 are the portions of region 502 that are imaged by the same pixels of a 2D projection of region 502 as high-contrast moving structure 501. For instance, in the 2D projection acquired at first image acquisition position 551, pixels 561 include image information from blocked portions 521 of region 502, and in the 2D projection acquired at second image acquisition position 552, pixels 562 include image information from blocked portions 522 of region 502. According to various embodiments described below, the effects of high-contrast moving structure 501 is visually removed from a reconstructed volume using 2D mask projections. The 2D mask projections are generated based on pixels associated with high-contrast moving structure 501, such as pixels 561 in the 2D projection acquired at image first acquisition position 551 and pixels 562 in the 2D projection acquired at second image acquisition position 552. To generate such a reconstructed volume, the visual information included in blocked portions 520 is approximated with 2D in-painted projections, in which pixels in the 2D mask projections that are associated with high-contrast moving structure 501 (e.g., pixels 561 or 562) are replaced with pixels generated via an in-painting process. One such embodiment is described below in conjunction with FIG. 6.

Figure 6:
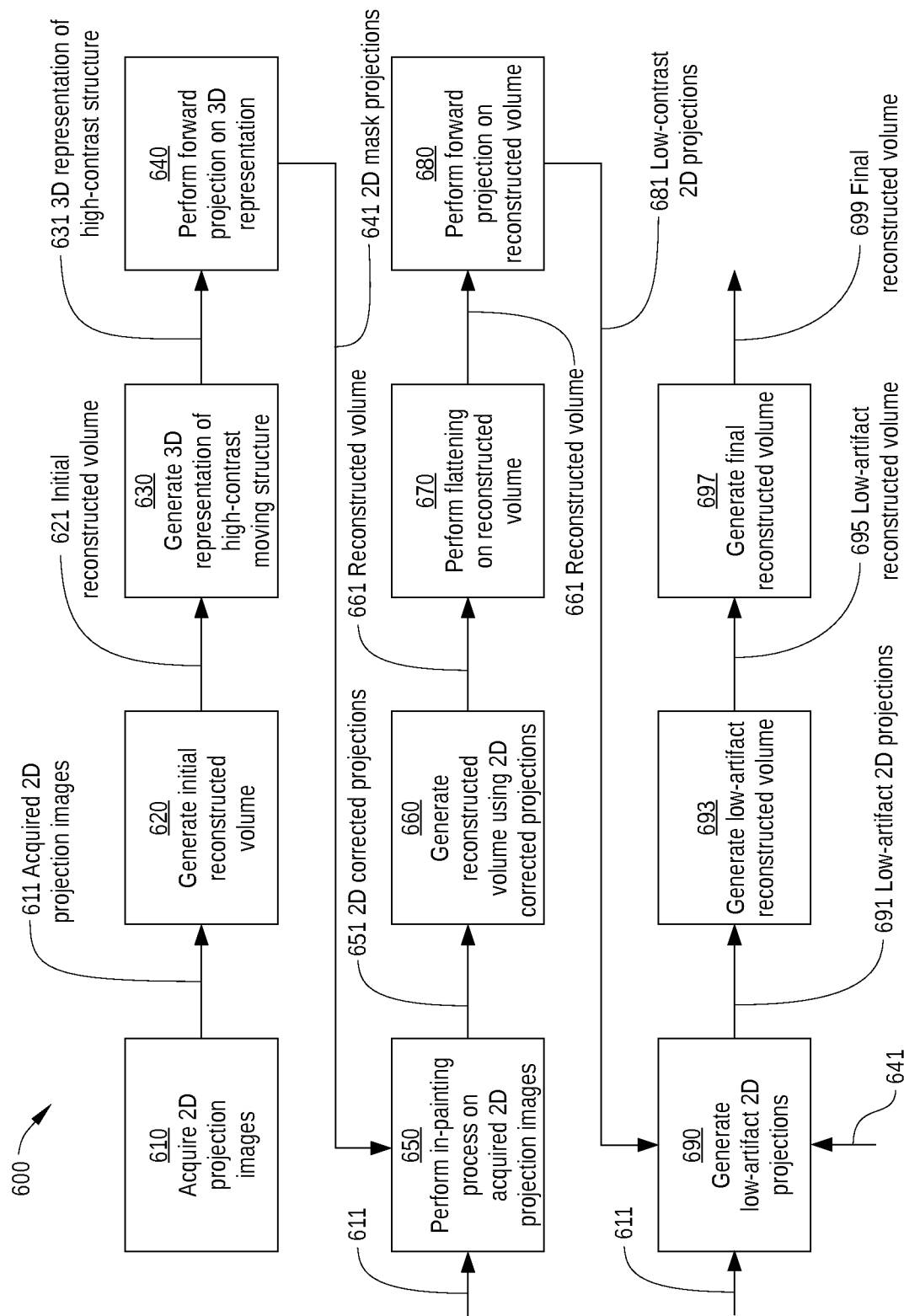
FIG. 6 sets forth a flowchart of a computer-implemented process for imaging a region of patient anatomy, according to one or more embodiments.

FIG. 6 sets forth a flowchart of a computer-implemented process 600 for imaging a region of patient anatomy, according to one or more embodiments. Computer-implemented process 600 can be implemented as an imaging-only process, or in conjunction with radiation therapy, such as IGRT, stereotactic radiosurgery (SRS), and the like. Further, computer-implemented process 600 may be performed over a single rotational arc of a gantry of a radiation therapy or imaging system, over a fraction of a rotational arc, or over multiple rotational arcs. Computer-implemented process 600 may include one or more operations, functions, or actions as illustrated by one or more of blocks 610-699. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented process 600 is described in conjunction with the X-ray imaging system described herein as part of radiation therapy system 100 and FIGS. 1-5, persons skilled in the art will understand that any suitably configured X-ray imaging system is within the scope of the present embodiments.

In step 610, the X-ray imaging system of radiation therapy system 100 acquires a set of acquired 2D projection images 611 of region 502, which includes target volume 209 and a high-contrast moving structure 501. Thus, region 502 includes a high-contrast moving portion (i.e., high-contrast moving structure 501).

In step 620, the X-ray imaging system generates an initial reconstructed volume 621 (first reconstructed volume) of region 502 based on acquired 2D projection images 611. Initial reconstructed volume 621 is a 3D volumetric data set of region 502. In some embodiments, a Feldkamp, Davis and Kress (FDK) reconstruction algorithm is employed to generate an initial reconstructed volume 621, and in other embodiments, any other suitable reconstruction algorithm is employed. It is noted that initial reconstructed volume 621 generally includes motion artifacts due to the presence of high-contrast moving structure 501 in region 502.

In step 630, the X-ray imaging system performs an autosegmentation of high-contrast moving structure 501 to generate a 3D representation 631 of high-contrast moving structure 501 disposed within region 502. 3D representation 631 includes 3D location information of high-contrast moving structure 501. Generally, the autosegmentation in step 630 is performed on initial reconstructed volume 621, and can be implemented via any suitable segmentation algorithm or software application configured to generate 3D location information of high-contrast moving structure 501. In alternative embodiments, the autosegmentation process of step 630 is performed directly on acquired 2D projection images 611. In such embodiments, 3D representation 631 of high-contrast moving structure 501 is then generated based on the location information included in the segmented acquired 2D projection images 611. In some embodiments, the segmentation algorithm employed in step 630 may be selected depending on the anatomical location within a patient target volume 209.

In some embodiments, an additional dilation procedure is performed on 3D representation 631, in which portions of region 502 that are immediately adjacent to high-contrast moving structure 501 are included in the 3D representation 631.

In step 640, the X-ray imaging system performs a forward projection process on 3D representation 631, to generate a set of 2D mask projections 641. Each 2D mask projection 641 in the set of 2D mask projections 641 includes location information indicating pixels that are blocked by high-contrast moving structure 501 during the forward projection process of step 640. In step 640, each 2D mask projection 641 generated is selected to correspond to a different acquired 2D projection image 611 included in the set of acquired 2D projection images 611 acquired in step 610. That is, for each 2D mask projection 641 generated in step 640, the forward projection process is performed using the same projection angle used to acquire one of acquired 2D projection images 611. Thus, each 2D mask projection 641 matches a corresponding acquired 2D projection image 611, and can be subsequently combined therewith, for example via the in-painting process of step 650 or the blending process of step 690.

In some embodiments, in step 640 an additional thresholding process is applied to each 2D mask projection 641. The thresholding process normalizes the pixels of a particular 2D mask projection 641 to be in the interval [0,1], where 1 corresponds to the contrast structure and 0 to the rest of region 502 (and therefore not a part of 2D projection mask 641).

In step 650, the X-ray imaging system performs an in-painting process on acquired 2D projection images 611 to generate a set of 2D corrected projections 651 of region 502. Specifically, each 2D corrected projection 651 is generated by modifying an acquired 2D projection image 611 based on the corresponding 2D mask projection, then in-painting replacement pixel information. In some embodiments, for a particular acquired 2D projection image 611, visual information (e.g., a pixel value) associated with high-contrast moving structure 501 is removed, based on location information included in the corresponding 2D mask projection 641. For example, in such an embodiment, pixel values for pixels that are indicated by the corresponding 2D mask projection to be associated with high-contrast moving structure 501 are removed from the particular acquired 2D projection image 611. Further, the removed visual information is replaced with lower-contrast pixel values via an in-painting process. For example, in some embodiments, a lower-contrast replacement pixel value for a pixel indicated by a 2D mask projection 641 to be associated with high-contrast moving structure 501 is generated by interpolating from pixel values for one or more pixels in the acquired 2D projection image 611 that are proximate to and/or adjacent to the pixel indicated by the 2D mask projection 641.

In step 660, the X-ray imaging system generates a reconstructed volume 661 (second reconstructed volume) of region 502 based on the 2D corrected projections 651 generated in step 650. In some embodiments, an FDK reconstruction algorithm is employed to generate reconstructed volume 661. In other embodiments, an algebraic reconstruction technique (ART) algorithm may be employed to generate reconstructed volume 661. Alternatively, any other suitable reconstruction algorithm can be employed in step 660. Reconstructed volume 661 is similar to initial reconstructed volume 621, except that high-contrast moving structure 501 has been removed.

In optional step 670, the X-ray imaging system performs a flattening process on reconstructed volume 661 to further reduce high-contrast artifacts and/or structures in reconstructed volume 661. In some embodiments, a simple thresholding method is employed in step 670, and in other embodiments, a filtering and/or convolutional neural network may also be employed in step 670.

In step 680, the X-ray imaging system performs a forward projection process on reconstructed volume 661 or on a post-processed (flattened) version of reconstructed volume 661, to generate a set of low-contrast 2D projections 681. It is noted that in each low-contrast 2D projection 681, pixels that are visually blocked by high-contrast moving structure 501 (i.e., pixels that are indicated by location information in a 2D mask projection to be associated with high-contrast moving structure 501) have pixel values that do not include a contribution from high-contrast moving structure 501. Instead, in each modified 2D projection 661, the pixel values for pixels that are visually blocked by high-contrast moving structure 501 are based on reconstructed volume 661, which is generated based on lower-contrast in-painted pixel values for pixels associated with high-contrast moving structure 501.

In step 680, each low-contrast 2D projection 681 generated is selected to correspond to a different acquired 2D projection image 611 included in the set of acquired 2D projection images 611 acquired in step 610. That is, for each low-contrast 2D projection 681 generated in step 680, the forward projection process is performed using the same projection angle used to acquire one of acquired 2D projection images 611. Thus, each low-contrast 2D projection 681 matches a corresponding acquired 2D projection image 611, and can be combined therewith subsequently, for example in the blending process of step 690.

In step 690, the X-ray imaging system generates a set of low-artifact 2D projections 691 of region 502 by modifying acquired 2D projection images 611 based on 2D projection masks 641 and low-contrast 2D projections 681. Specifically, location information from 2D projection masks 641 indicates certain pixels of acquired 2D projection images 611 that are to have image information (e.g., pixel values) replaced with image information from corresponding pixels of low-contrast 2D projections 681. It is noted that in general, the majority of pixels of low-artifact 2D projections 691 have the same pixel values and/or other image information as the corresponding pixels of acquired 2D projection images 611. However, the pixels of low-artifact 2D projections 691 that are indicated by location information in 2D projection masks 641 to be blocked by or associated with high-contrast moving structure 501 include pixel values and/or other image information that are different from the corresponding pixels of low-contrast 2D projections 681.

In some embodiments, to minimize or otherwise reduce visual artifacts caused by replacing image information for groups of pixels in acquired 2D projection images 611, certain pixels in low-artifact 2D projections 691 (referred to herein as "scaled pixels") include scaled image information. In such embodiments, the scaled pixels are disposed in edge regions of low-artifact 2D projections 691 that border regions of low-artifact 2D projections 691 that include replaced image information. For example, in some embodiments, the edge regions of low-artifact 2D projections 691 include one or more pixels with image information from pixels of acquired 2D projection images 611 and one or more pixels with image information from pixels of low-contrast 2D projections 681. In such embodiments, the scaled pixels include image information that is based on image information from pixels of acquired 2D projection images 611 and on image information from pixels of low-contrast 2D projections 681. In some embodiments, each scaled pixel includes image information that is scaled between image information from one or more pixels of acquired 2D projection images 611 and image information from one or more pixels of low-contrast 2D projections 681. As a result, visual artifacts and/or other inconsistencies are avoided when image information in certain pixels of acquired 2D projection images 611 is replaced.

In step 693, the X-ray imaging system executes a reconstruction algorithm using the set of low-artifact 2D projections 691 of region 502 to generate a low-artifact reconstructed volume 695 (third reconstructed volume) of region 502. Thus, the X-ray imaging system generates low-artifact reconstructed volume 695 of region 502 based on the low-artifact 2D projections 691 generated in step 690. In some embodiments, an FDK reconstruction algorithm is employed to generate low-artifact reconstructed volume 695. In other embodiments, an ART algorithm may be employed to low-artifact reconstructed volume 695. In other embodiments, a penalized-likelihood (PL) reconstruction algorithm is employed to generate low-artifact reconstructed volume 695. Alternatively, any other suitable reconstruction algorithm can be employed in step 690. Low-artifact reconstructed volume 695 is similar to initial reconstructed volume 621, except that high-contrast moving structure 501 has been removed and artifacts caused by the presence of high-contrast moving structure 501 have been removed and/or reduced in visual prominence.

In step 697, the X-ray imaging system generates a final reconstructed volume 699 (fourth reconstructed volume) of region 502. In step 697, the X-ray imaging system blends low-artifact reconstructed volume 695 with image information (e.g., pixel values) from 3D representation 631 of high-contrast moving structure 501. In some embodiments, the pixels that are modified with image information from 3D representation 631 are indicated by location information included in 3D representation 631.

Figure 7:
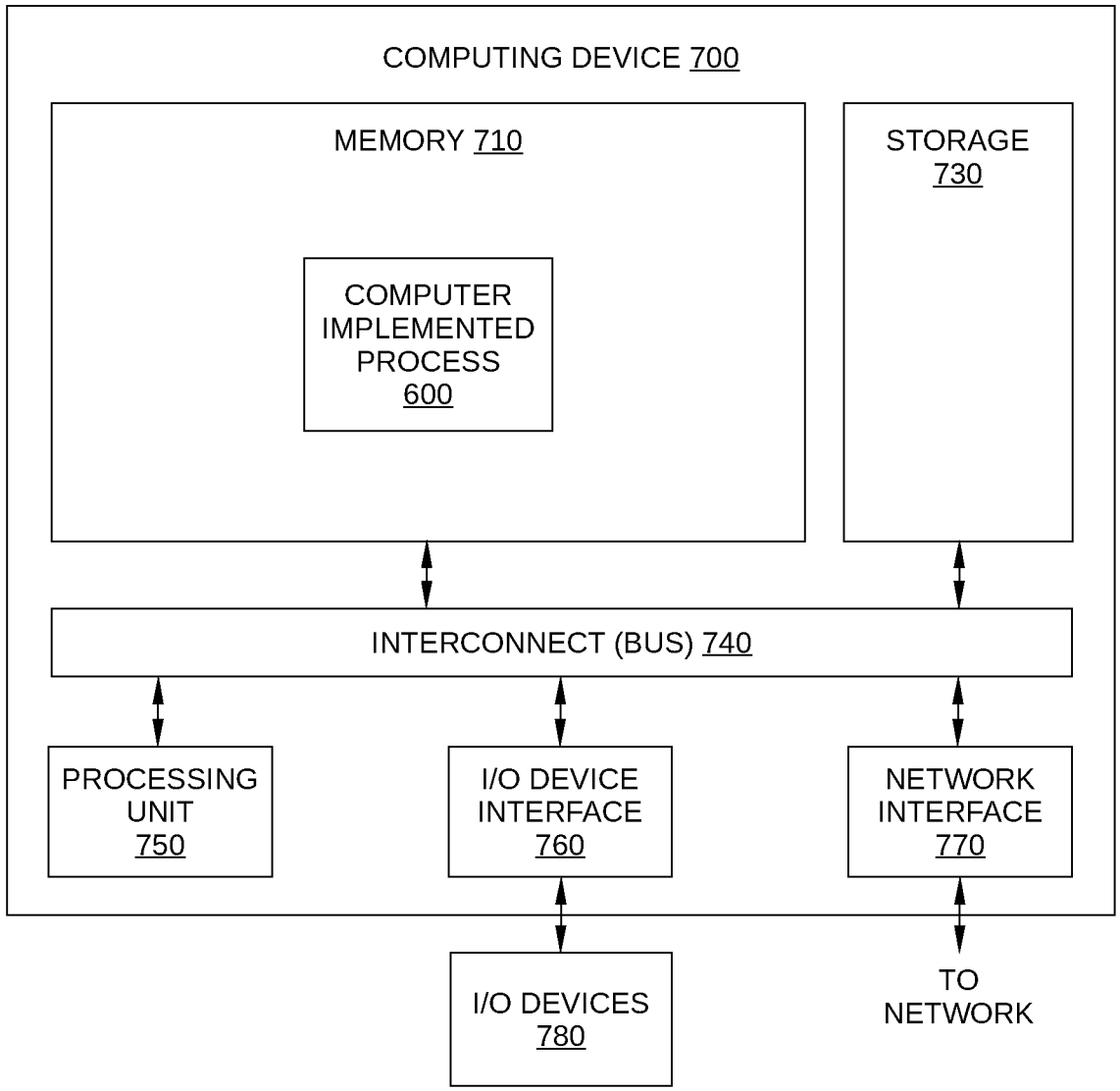
FIG. 7 is an illustration of a computing device configured to perform various embodiments of the present disclosure.

FIG. 7 is an illustration of computing device 700 configured to perform various embodiments of the present disclosure. Computing device 700 may be a desktop computer, a laptop computer, a smart phone, or any other type of computing device suitable for practicing one or more embodiments of the present disclosure. In operation, computing device 700 is configured to execute instructions associated with patient training phase 501, dosimetric analysis phase 502, and/or treatment fraction process 1100 as described herein. It is noted that the computing device described herein is illustrative and that any other technically feasible configurations fall within the scope of the present disclosure.

As shown, computing device 700 includes, without limitation, an interconnect (bus) 740 that connects a processing unit 750, an input/output (I/O) device interface 760 coupled to input/output (I/O) devices 780, memory 710, a storage 730, and a network interface 770. Processing unit 750 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 750 may be any technically feasible hardware unit capable of processing data and/or executing software applications, including computer-implemented process 600.

I/O devices 780 may include devices capable of providing input, such as a keyboard, a mouse, a touch-sensitive screen, and so forth, as well as devices capable of providing output, such as a display device and the like. Additionally, I/O devices 780 may include devices capable of both receiving input and providing output, such as a touchscreen, a universal serial bus (USB) port, and so forth. I/O devices 780 may be configured to receive various types of input from an end-user of computing device 700, and to also provide various types of output to the end-user of computing device 700, such as displayed digital images or digital videos. In some embodiments, one or more of I/O devices 780 are configured to couple computing device 700 to a network.

Memory 710 may include a random access memory (RAM) module, a flash memory unit, or any other type of memory unit or combination thereof. Processing unit 750, I/O device interface 760, and network interface 770 are configured to read data from and write data to memory 710. Memory 710 includes various software programs that can be executed by processor 750 and application data associated with said software programs, including computer-implemented process 600.

Figure 8:
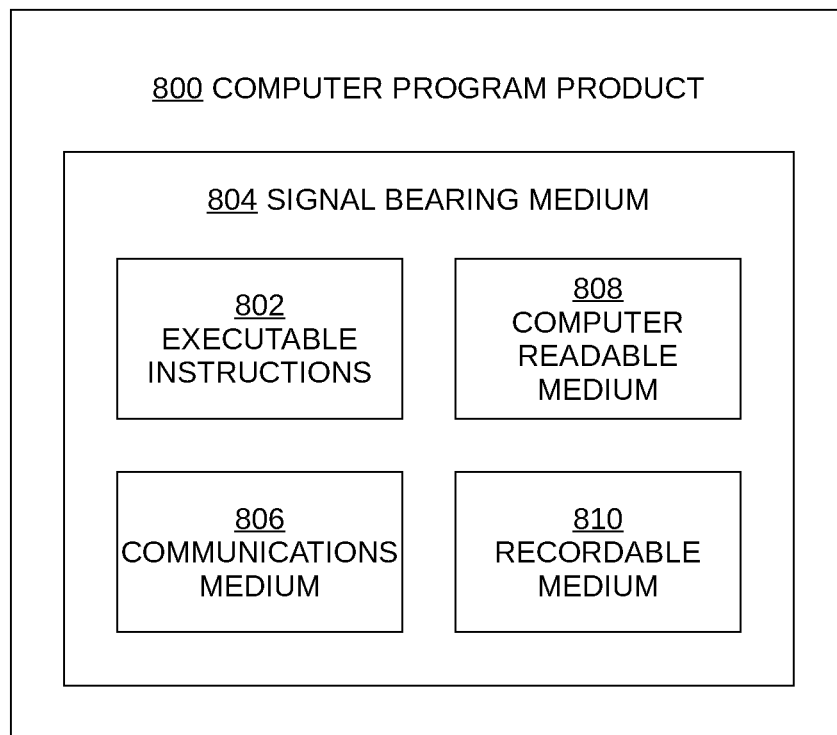
FIG. 8 is a block diagram of an illustrative embodiment of a computer program product for implementing one or more embodiments of the present disclosure.

FIG. 8 is a block diagram of an illustrative embodiment of a computer program product 800 for implementing a method for segmenting an image, according to one or more embodiments of the present disclosure. Computer program product 800 may include a signal bearing medium 804. Signal bearing medium 804 may include one or more sets of executable instructions 802 that, when executed by, for example, a processor of a computing device, may provide at least the functionality described above with respect to FIGS. 1-7.

In some implementations, signal bearing medium 804 may encompass a non-transitory computer readable medium 808, such as, but not limited to, a hard disk drive, a Compact Disc (CD), a Digital Video Disk (DVD), a digital tape, memory, etc. In some implementations, signal bearing medium 804 may encompass a recordable medium 810, such as, but not limited to, memory, read/write (R/W) CDs, R/W DVDs, etc. In some implementations, signal bearing medium 804 may encompass a communications medium 806, such as, but not limited to, a digital and/or an analog communication medium (e.g., a fiber optic cable, a waveguide, a wired communications link, a wireless communication link, etc.). Computer program product 800 may be recorded on non-transitory computer readable medium 808 or another similar recordable medium 810.

In sum, embodiments described herein reduce and/or eliminate motion artifacts that occur around moving high-contrast portions of patient anatomy. Further, in some instances, the embodiments reveal structures previously covered by such motion artifacts. Thus, the embodiments improve the perceived image quality of CBCT-based reconstructions and, in some instances improve accuracy in differentiating tissue types in a reconstructed CBCT image. Such improvements over prior art techniques may be employed in adaptive planning and/or during radiation therapy.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:
1. A computer-implemented method of imaging a region of patient anatomy that includes a target volume, the method comprising:
    performing an autosegmentation of a high-contrast portion of a first reconstructed volume of the region to generate a three-dimensional (3D) representation of the high-contrast portion disposed within the region, wherein the first reconstructed volume is reconstructed based on a set of two-dimensional (2D) acquired projections of the region;
    generating a set of 2D mask projections of the region by performing a forward projection process on the 3D representation, wherein each 2D mask projection in the set of 2D mask projections includes location information indicating pixels that are blocked by the high-contrast portion during the forward projection process performed on the 3D representation;
    based on the set of 2D acquired projections and the location information, generating a set of 2D corrected projections of the region, wherein each 2D corrected projection in the set of 2D corrected projections is generated by removing visual information associated with the high-contrast portion from a corresponding 2D acquired projection in the set of 2D acquired projections;
    generating a second reconstructed volume of the region based on the 2D corrected projections;
    generating a set of low-contrast 2D projections of the region by performing a forward projection process on the second reconstructed volume; and
    generating a third reconstructed volume of the region by:
        generating a set of low-artifact 2D projections of the region by replacing image information for certain pixels in one or more of the 2D acquired projections with image information from corresponding pixels in the low-contrast 2D projections; and
        executing a reconstruction algorithm using the set of low-artifact 2D projections of the region to generate the third reconstructed volume.

2. The computer-implemented method of claim 1, wherein the corresponding pixels in the low-contrast 2D projections are indicated by the location information.

3. The computer-implemented method of claim 1, further comprising blending the third reconstructed volume with image information from the 3D representation that corresponds to the high-contrast portion to generate a fourth reconstructed volume.

4. The computer-implemented method of claim 1, wherein the 3D representation includes location information of the high-contrast portion generated by the autosegmentation of the high-contrast portion.

5. The computer-implemented method of claim 1, wherein the high-contrast portion comprises at least one of a gas bubble or a fiducial marker disposed within the region.

6. The computer-implemented method of claim 1, further comprising, causing the set of acquired 2D projections of the region to be acquired prior to performing the autosegmentation of the high-contrast portion.

7. The computer-implemented method of claim 6, wherein causing the set of acquired 2D projections to be acquired comprises:
    causing a first 2D projection of the region to be acquired while the high-contrast portion is disposed in a first position within the region; and
    causing a second 2D projection of the region to be acquired while the high-contrast portion is disposed in a second position within the region.

8. The computer-implemented method of claim 1, further comprising, reconstructing a fourth reconstructed volume of the region based on the 2D corrected projections.

9. The computer-implemented method of claim 8, wherein reconstructing the fourth reconstructed volume is further based on image information from the 2D mask projections.

10. A non-transitory computer-readable storage medium including instructions that, when executed by one or more processors, configure the one or more processors to perform the steps of:
   performing an autosegmentation of a high-contrast portion of a first reconstructed volume of the region to generate a three-dimensional (3D) representation of the high-contrast portion disposed within the region, wherein the first reconstructed volume is reconstructed based on a set of two-dimensional (2D) acquired projections of the region;
   generating a set of 2D mask projections of the region by performing a forward projection process on the 3D representation, wherein each 2D mask projection in the set of 2D mask projections includes location information indicating pixels that are blocked by the high-contrast portion during the forward projection process performed on the 3D representation;
   based on the set of 2D acquired projections and the location information, generating a set of 2D corrected projections of the region, wherein each 2D corrected projection in the set of 2D corrected projections is generated by removing visual information associated with the high-contrast portion from a corresponding 2D acquired projection in the set of 2D acquired projections;
   generating a second reconstructed volume of the region based on the 2D corrected projections
   generating a set of low-contrast 2D projections of the region by performing a forward projection process on the second reconstructed volume; and
   generating a third reconstructed volume of the region by:
      generating a set of low-artifact 2D projections of the region by replacing image information for certain pixels in one or more of the 2D acquired projections with image information from corresponding pixels in the low-contrast 2D projections; and
      executing a reconstruction algorithm using the set of low-artifact 2D projections of the region to generate the third reconstructed volume.

11. The non-transitory computer-readable storage medium of claim 10, wherein the corresponding pixels in the low-contrast 2D projections are indicated by the location information.

12. The non-transitory computer-readable storage medium of claim 11, further including instructions that, when executed by one or more processors, configure the one or more processors to perform the step of blending the third reconstructed volume with image information from the 3D representation that corresponds to the high-contrast portion to generate a fourth reconstructed volume.

13. The non-transitory computer-readable storage medium of claim 10, wherein the 3D representation includes location information of the high-contrast portion generated by the autosegmentation of the high-contrast portion.

14. The non-transitory computer-readable storage medium of claim 10, wherein the high-contrast portion comprises at least one of a gas bubble or a fiducial marker disposed within the region.

15. The computer-implemented method of claim 10, further including instructions that, when executed by one or more processors, configure the one or more processors to perform the step of causing the set of acquired 2D projections of the region to be acquired prior to performing the autosegmentation of the high-contrast portion.

16. The computer-implemented method of claim 15, wherein causing the set of acquired 2D projections to be acquired comprises:
   causing a first 2D projection of the region to be acquired while the high-contrast portion is disposed in a first position within the region; and
   causing a second 2D projection of the region to be acquired while the high-contrast portion is disposed in a second position within the region.

17. The computer-implemented method of claim 10, further including instructions that, when executed by one or more processors, configure the one or more processors to perform the step of reconstructing a fourth reconstructed volume of the region based on the 2D corrected projections.

18. The computer-implemented method of claim 17, wherein reconstructing the fourth reconstructed volume is further based on image information from the 2D mask projections.

* * * * *